(12) United States Patent
Henning et al.

(10) Patent No.: US 8,864,882 B2
(45) Date of Patent: Oct. 21, 2014

(54) INLINE WATER TRAP

(71) Applicant: Criticare Systems, Inc., Waukesha, WI (US)

(72) Inventors: Roy Henning, Hartford, WI (US); Daniel Schwarz, Hartland, WI (US); Deborah Zane, Monona, WI (US)

(73) Assignee: Criticare Systems, Inc., Waukesha, WI (US)

( * ) Notice: Subject to any disclaimer, the term of this patent is extended or adjusted under 35 U.S.C. 154(b) by 0 days.

(21) Appl. No.: 14/067,361

(22) Filed: Oct. 30, 2013

(65) Prior Publication Data
US 2014/0058281 A1 Feb. 27, 2014

Related U.S. Application Data

(63) Continuation of application No. 13/858,522, filed on Apr. 8, 2013, now Pat. No. 8,597,403, which is a continuation of application No. 13/032,469, filed on Feb. 22, 2011, now Pat. No. 8,414,682.

(60) Provisional application No. 61/306,769, filed on Feb. 22, 2010.

(51) Int. Cl.
*B01D 46/30* (2006.01)
*A61M 16/08* (2006.01)
*B01D 53/38* (2006.01)
*B01D 53/26* (2006.01)
*B01D 53/04* (2006.01)
*A61B 5/08* (2006.01)
*A61M 16/10* (2006.01)
*A61B 5/097* (2006.01)
*A61B 5/087* (2006.01)
*A61B 5/091* (2006.01)

(52) U.S. Cl.
CPC ............. *A61B 5/097* (2013.01); *B01D 2257/80* (2013.01); *A61M 2205/7536* (2013.01); *A61M 16/0808* (2013.01); *B01D 53/38* (2013.01); *B01D 53/261* (2013.01); *A61M 2205/7527* (2013.01); *A61B 5/087* (2013.01); *B01D 2259/4533* (2013.01); *B01D 53/0454* (2013.01); *B01D 2258/06* (2013.01); *A61B 5/082* (2013.01); *A61M 16/085* (2013.01); *A61B 5/091* (2013.01); *A61M 16/106* (2013.01)
USPC .................. 96/25; 95/117; 55/385.1; 55/394; 55/482; 55/495; 55/498; 96/109; 96/118

(58) Field of Classification Search
USPC ............. 95/25, 117; 55/385.1, 394, 482–486, 55/495, 498; 96/25, 109, 118
See application file for complete search history.

(56) References Cited

U.S. PATENT DOCUMENTS 6,041,777 A * 3/2000 Faithfull et al. .......... 128/200.24
7,621,171 B2 * 11/2009 O'Brien ....................... 73/23.41
(Continued)

*Primary Examiner* — Jason M Greene
*Assistant Examiner* — Karla Hawkins
(74) *Attorney, Agent, or Firm* — Factor Intellectual Property Law Group, Ltd.

(57) ABSTRACT

An inline water trap including a filter component and a panel connector configured to interface with a patient gas monitor. In one embodiment the inline water trap indicates to the patient gas monitor that it is in place and that the patient gas monitor may begin intaking and analyzing the filtered patient sample. The inline water trap receives a patient sample and filters water and contaminants from the sample before allowing the remaining gas portion of the sample to pass through to the patient gas monitor, thereby protecting the patient gas monitor from damage. One embodiment of the inline water trap additionally contains an RFID tag to indicate to the patient gas monitor that the correct type of inline water trap is engaged.

20 Claims, 15 Drawing Sheets

(56) References Cited

U.S. PATENT DOCUMENTS

2007/0271997 A1* 11/2007 O'Brien ................. 73/23.37
2011/0247620 A1* 10/2011 Armstrong et al. ...... 128/204.23
2011/0283884 A1* 11/2011 Larsen et al. ................. 95/25
2012/0000462 A1* 1/2012 Edwards et al. ......... 128/201.21
2013/0220129 A1* 8/2013 Henning et al. ............. 96/109

* cited by examiner

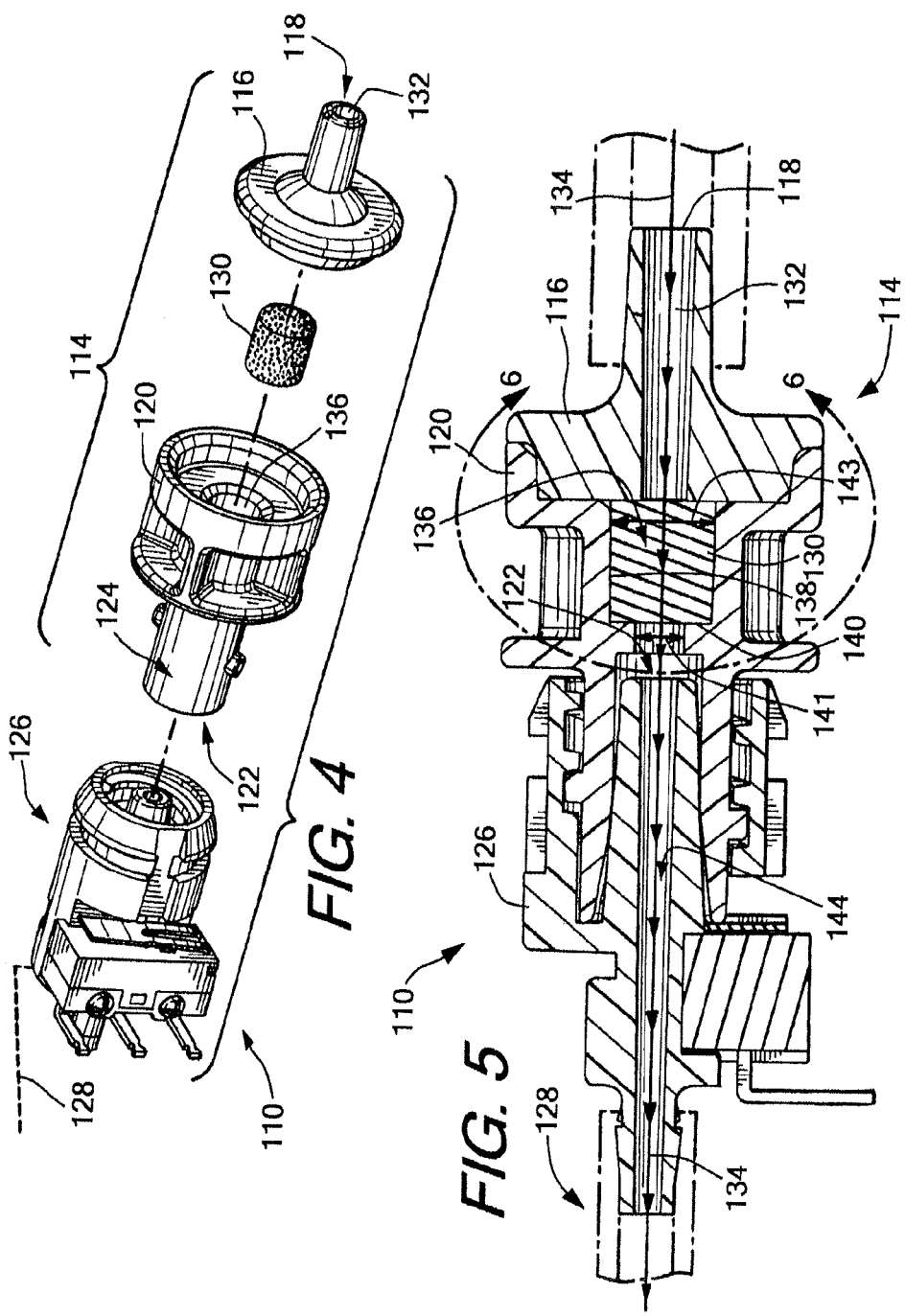

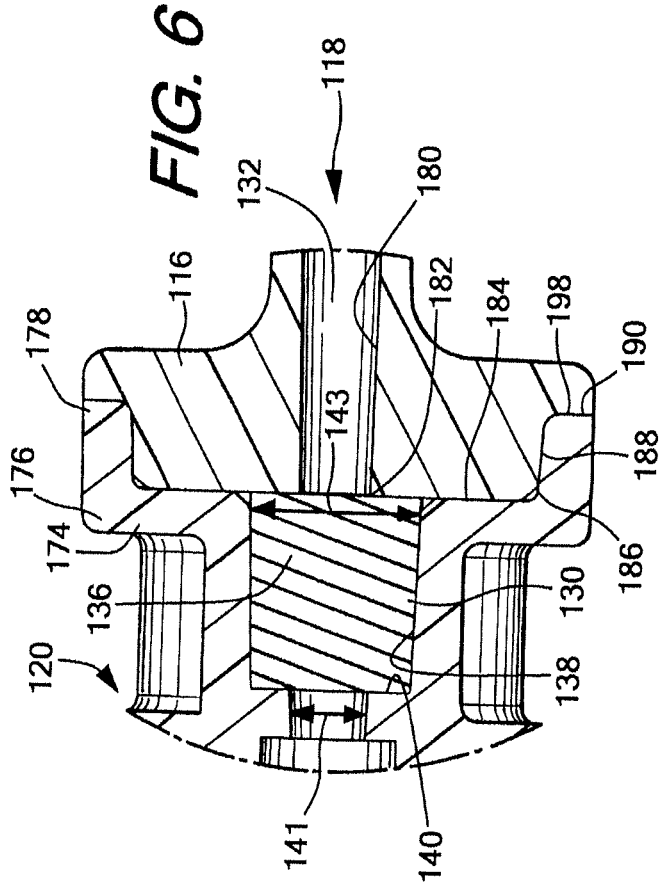

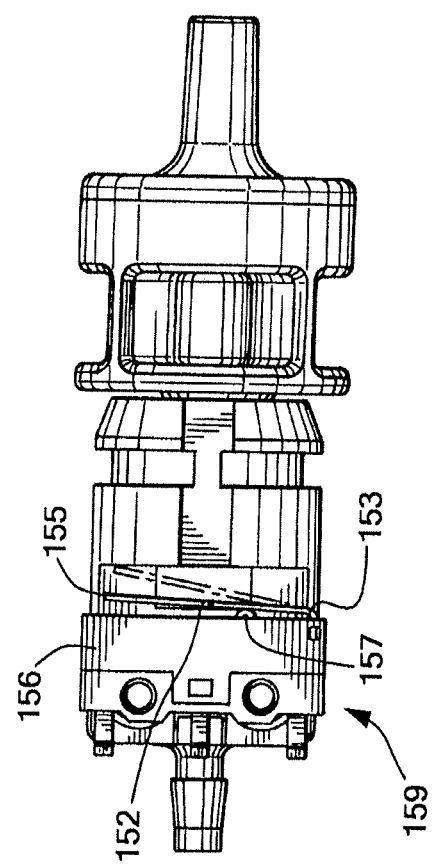

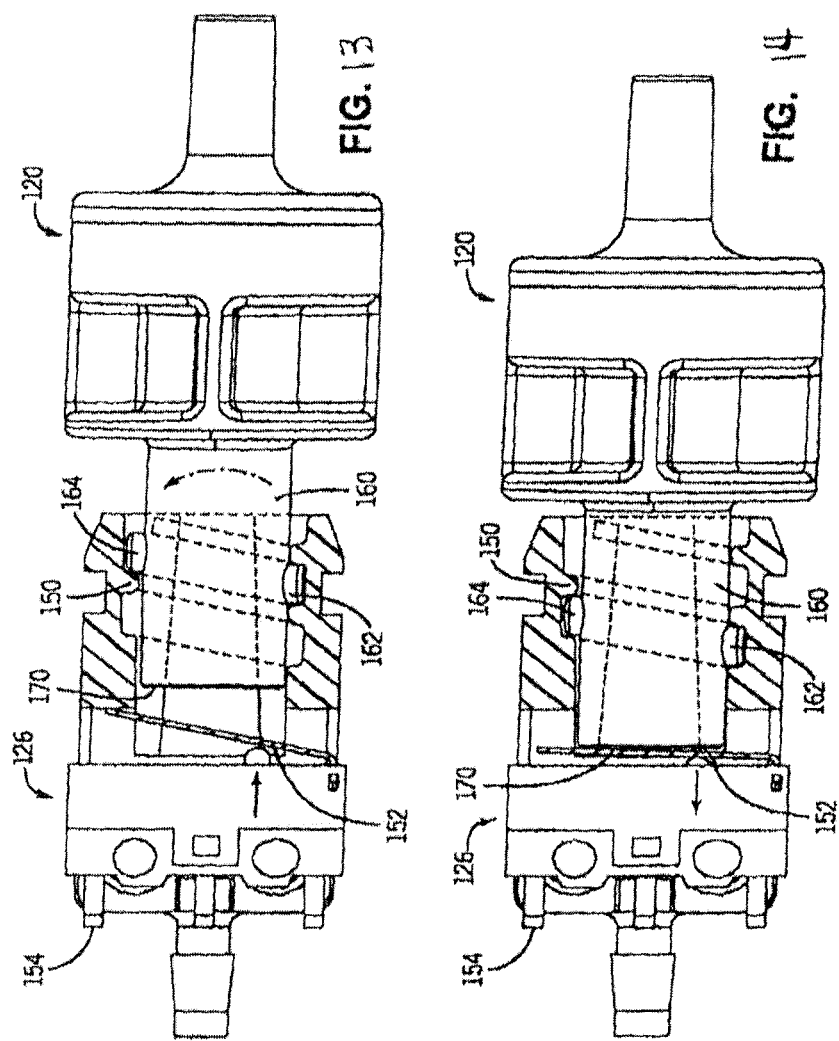

INLINE WATER TRAP

This application is a continuation of U.S. patent application Ser. No. 13/858,522, filed on Apr. 8, 2013 which is a continuation of U.S. patent application Ser. No. 13/032,469 (now U.S. Pat. No. 8,414,682), filed on Feb. 22, 2011 which claims the benefit of U.S. Provisional Patent Application No. 61/306,769, filed on Feb. 22, 2010—the contents of each of these applications are incorporated herein by reference in their entirety.

BACKGROUND OF THE INVENTION

Field of the Invention

The present invention relates generally to gas/liquid separators for use with respiratory gas monitors or analyzers, and more particularly, to an inline water trap for removing liquid and other contaminants from a respiratory sample.

Respiratory gas analyzers monitor exhaled air from a patient. It has long been recognized that means must be provided for removing excess moisture from the exhaled air prior to analysis. One technique for removing excess moisture from respiratory gas samples utilizes the effects of surface tension and capillary action to separate water from gas samples. Know gas/liquid separators, or water traps, employing this technique include a separation chamber which has a geometrical configuration designed to draw water away from a gas sample outlet and direct the water to a collection chamber. Examples of such prior art water traps are disclosed in U.S. Pat. Nos. 4,579,568 and 4,713,095 to Riciardelli. However, these prior art water traps can become filled, and the sample inlet line that conducts exhaled air to the water trap can become blocked with condensed moisture.

Another water trap, disclosed in U.S. Pat. No. 4,924,860, employs a separation chamber having a geometrical configuration similar to the one disclosed in U.S. Pat. No. 4,713,095. This water trap additionally includes self-sealing filters which positively seal the exit ports of the water trap in the even the water trap becomes over filled and can no longer perform its water trap function. In one embodiment, one self-sealing filter is disposed in a sample outlet conduit and a further self-sealing filter is disposed in a vacuum conduit. The self-sealing filters comprise a porous matrix including means for rendering the porous matrix substantially non-porous when exposed to water, thereby blocking the exit ports of the water trap.

In applications for "dry" patient samples, which do not warrant a water tank or collection chamber, the presence of such water tank or collection chamber can result in dead spaces, thereby minimizing response time for the respiratory gas monitor.

Additionally, water traps having a water tank or collection chamber generally are not suitable for single-patient use, wherein the water are disposed of after each use.

Accordingly, it is an objective of the present invention to provide an inline water trap for separating liquid and contaminants containing water from a patient respiratory gas sample, prior to supplying the patient sample to a respiratory gas analyzer.

Another objective of the invention is for the respiratory gas analyzer to be enabled to operate only when a filtered sample is present.

It is a further objective of the invention to provide for the respiratory gas analyzer to can be activated when the correct type of filter is present to filter the patient sample prior to the patient sample entering the respiratory gas analyzer for analysis.

It is a further objective to provide a water trap that minimizes dead space, therefore, minimizing response time of a respiratory gas monitor.

It is a further objective to provide a water trap suitable for use in applications involving "dry" patient samples.

It is another objective of the invention to provide a disposable water trap that is inexpensive, making it suitable for single patient use.

It is another objective of the invention to provide an inline water trap including both a hydrophilic pellet and a hydrophobic filter to further prevent water and water containing contaminants from reaching the respiratory gas monitor.

The inline water trap of the present invention must also be of a construction which is both durable and long lasting, and it should also require little or no maintenance to be provided by the user throughout its operating lifetime. In order to enhance the market appeal of the inline water trap of the present invention, the inline water trap should also be of relatively inexpensive construction to thereby afford it the broadest possible market. Finally, it is also an objective that all of the aforesaid advantages and objectives of the inline water trap of the present invention be achieved without incurring any substantial relative disadvantage.

SUMMARY OF THE INVENTION

An embodiment of the invention may provide an inline water trap which may be used with respiratory gas monitors for removing liquid and other contaminants and liquid containing contaminants from patient samples prior to supplying the patient samples to the gas monitoring and detection elements of the respiratory gas monitor.

In one embodiment an inline water trap can include a panel connector of a respiratory gas monitor. The inline water trap can include a filter component defining a bore. The filter component can include a filter body. The filter body can include a filter inlet and a filter outlet in fluid communication through the bore. The filter component can include a panel connector engagement portion. The filter component can include a filter element, in one embodiment in the form of a hydrophilic pellet, which may be disposed within the bore and may be configured to allow gas to pass through the bore while preventing at least one of water and contaminants from passing through the bore. The panel connector may define a filter component engagement portion. The filter component engagement portion can be configured to selectively engage the panel connector engagement portion of the filter component for securing the filter component to the panel connector. The inline water trap can include a sensing arrangement including first and second cooperative elements. The first and second cooperative elements can provide operative communication between the filter component and the respiratory gas monitor to enable gas monitoring and detecting components of the respiratory gas monitor to operate when the filter component is engaged with the panel connector.

In one embodiment the sensing arrangement can comprise mechanical communication between the filter component and the panel connector. In another embodiment the first cooperative element can comprise the filter body end wall, and the second cooperative element can comprise a switching mechanism of the panel connector.

In another embodiment, the sensing arrangement can comprise wireless communication between the filter component and the panel connector. In another embodiment the first cooperative element can comprise an RF tag coupled to the filter component, and the second cooperative element can comprise an RF sensor in communication with the respiratory gas monitor.

An embodiment of an inline water trap can provide a patient sample filtered of at least one of water and contaminants to a respiratory gas monitor is provided. The inline water trap can include a filter component. The filter component can define a bore. The inline water trap also can include a panel connector. The panel connector can include a switching mechanism for indicating to the respiratory gas monitor that the filter component is engaged with the panel connector. The filter component can include a filter inlet in fluid communication with a filter outlet through the bore. The filter component also can include a filter disposed between the filter inlet and the filter outlet. The filter component can be configured to cause the actuation of the switching mechanism whenever the filter component is engaged with the panel connector.

In another embodiment the filter component can define a tubular panel connector engagement portion configured to threadingly couple with the panel connector.

In another embodiment the tubular panel connector engagement portion can include a pair of radially oppositely projecting projections configured to cooperatively selectively engage a threading defined by the panel connector.

In one embodiment the switching mechanism can include a switch lever. The tubular panel connector can depress the switch lever when the filter component is engaged with the panel connector.

In another embodiment one of the panel connector and the respiratory gas monitor can include an RFID sensor. The filter component can include an RFID tag. The RFID sensor can be configured to sense the presence of the RFID tag and can indicate when the RFID tag is sensed.

In another embodiment an inline water trap for providing a filtered patient sample to a respiratory gas monitor can be provided. The inline water trap can include a filter body defining a bore. The bore can have an axis. The filter body can include a filter inlet and a filter outlet. The inline water trap can include a filter disposed within the bore. The filter can be configured to allow gas to pass through the bore but to prevent liquid from passing through the bore. The filter body can be positioned in operative communication with the respiratory gas monitor to provide a filtered patient sample to the respiratory gas monitor. The filter body can cause the respiratory gas monitor to be alerted when the filter body is positioned to provide a filtered patient sample to the respiratory gas monitor. A patient sample can travel coaxially with the axis through the filter body.

In one embodiment the panel connector can have an axis that extends coaxially with the axis of the filter body.

In another aspect, an embodiment of the present invention can provide a method of providing a filtered patient sample to a respiratory gas monitor. The method can include providing a filter component configured to receive a patient sample. The method can include coupling the filter component to a panel connector in operative communication with the respiratory gas monitor to provide a filtered patient sample from the filter component to the respiratory gas monitor. The method can include indicating to the respiratory gas monitor that the filter component is coupled to the panel connector. The method can include filtering at least one of water and contaminants from a patient sample. The method can include providing the filtered patient sample to the respiratory gas monitor.

Advantageously, an embodiment of the inline water trap of the present invention can filter the patient sample of water and/or contaminants prior to the patient sample entering the respiratory gas analyzer.

Further, an embodiment of the inline water trap of the present invention can enable the respiratory gas monitor to operate only when the filter component of the inline water trap is properly engaged with a panel connector of the respiratory gas monitor, and can protect the respiratory gas monitor from intaking water or other contaminants either from the environment or from an unfiltered patient sample.

Additionally, an embodiment of the inline water trap of the present invention can be recognizable by the respiratory gas monitor such that the respiratory gas monitor can be enabled to operate only when the correct type of inline water trap is engaged with the respiratory gas monitor.

An embodiment of the inline water trap of the present invention can minimize dead space, therefore, minimizing response time.

An embodiment of the inline water trap of the present invention can be useful for filtering patient samples with low amounts of water and contaminants and can eliminate the need for a collection tank or chamber.

An embodiment of the inline water trap of the present invention can be a disposable item suitable for single patient use.

An embodiment of the inline water trap of the present invention can include both a hydrophilic pellet and a hydrophobic filter to further prevent water and other water containing contaminants from reaching the respiratory gas monitor.

An embodiment of the inline water trap of the present invention can be of a construction which is both durable and long lasting, and can also require little or no maintenance to be provided by the user throughout its operating lifetime. An embodiment of the inline water trap of the present invention can also be of relatively inexpensive construction to enhance its market appeal and to thereby afford it the broadest possible market. Finally, an embodiment of the inline water trap of the present invention can achieve all of the aforesaid advantages and objectives without incurring any substantial relative disadvantage.

DESCRIPTION OF THE DRAWINGS

These and other advantages of the present invention are best understood with reference to the drawings, in which:

FIG. 2 is a flow diagram illustrating operational logic controlling a function of the respiratory gas monitor to which an embodiment of the inline water trap of the present invention is configured to provide a sample to;

FIG. 4 is an exploded view of an embodiment of an inline water trap of the present invention illustrated in FIGS. 1 and 3;

FIG. 5 is a side cross-sectional view of the inline water trap illustrated in FIGS. 1, 3, and 4, including the panel connector, illustrating flow through the inline water trap;

FIG. 6 is a magnified cross-sectional view of the connection between the filter body and the filter input of an embodiment of the inline water trap of FIGS. 1 and 3-5;

FIG. 12 is a top view of an embodiment of the inline water trap illustrating actuating of the switch lever;

FIG. 13 is a partial cross-sectional view showing the filter body portion engaging the panel connector of an embodiment of the inline water trap prior to actuating the switch lever;

FIG. 14 is a partial cross-sectional view showing the filter body portion engaged with the panel connector of an embodiment of the inline water trap as it actuates the switch lever;

DETAILED DESCRIPTION OF THE EXEMPLARY EMBODIMENTS

Figure 1:
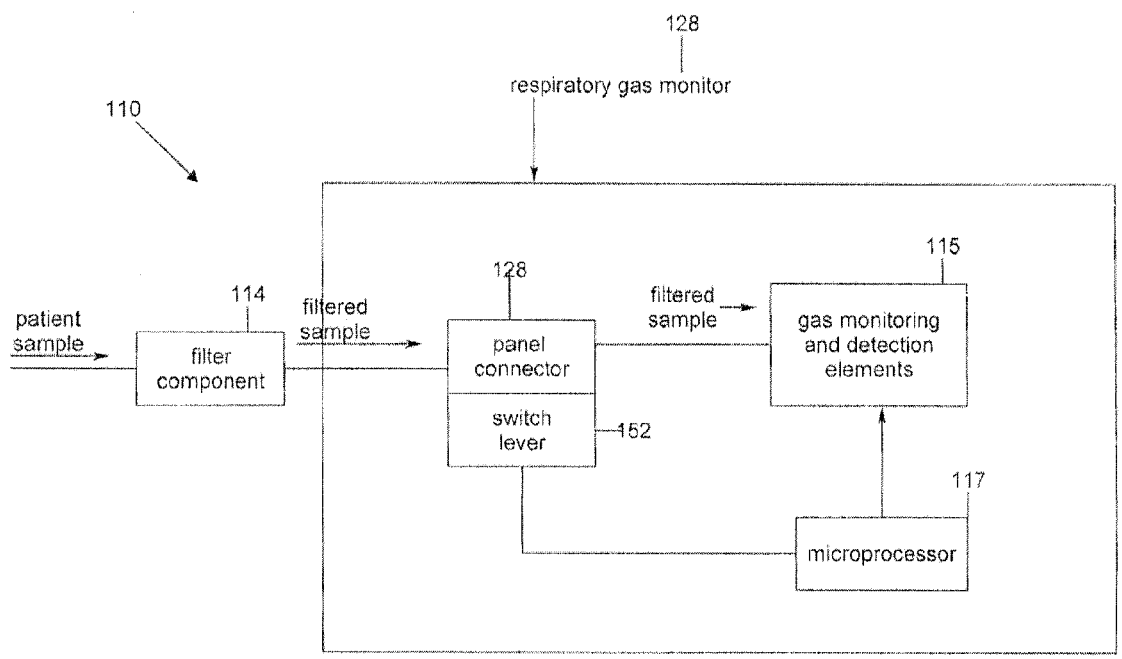
FIG. 1 is a system block diagram showing an embodiment of the inline water trap of the present invention coupled to a respiratory gas monitor.

Referring to the drawings, FIG. 1 illustrates a respiratory gas monitoring system including an inline water trap 110 in accordance with the present invention. The inline water trap 110 includes a filter component 114 and a panel connector 126. The panel connector 126 is mounted on or in a respiratory gas monitor 128. The filter component 114 of the inline water trap 110 is configured to couple with the panel connector 126. The inline water trap 110 blocks the passage of any water or other contaminants from a patient sample, while allowing the passage of respiratory gases from patients. Thus, the inline water trap 110 separates liquid or contaminants that contain water from the patient sample and passes the filtered patient sample to gas monitoring and detection components 115 of the respiratory gas monitor 128.

In accordance with an embodiment of the present invention, the inline water trap 110 includes a protection arrangement that ensures that patient samples are being supplied to the respiratory gas monitor 128 through a proper water trap to the prevent degradation or failure of the gas monitoring and detection components of the respiratory gas monitor 128. In one embodiment, this function is implemented by the use of a proprietary connection arrangement that is compatible with products made by Criticare Systems, Inc., located at N7W22025 Johnson Dr., Waukesha, Wis. 53186.

In one embodiment, the inline water trap 110 includes a sensing arrangement 101 (see FIG. 2) that allows a microprocessor 117 of the respiratory gas monitor 128 to determine when a proper water trap is connected to the respiratory gas monitor before enabling the gas monitoring and detection components 115 to begin monitoring and analyzing a patient sample. Various sensing arrangements, indication mechanisms, or switching mechanisms for indicating to the gas monitoring and detection components 115 that they may begin monitoring and analyzing a filtered patient sample are envisioned. Some exemplary mechanisms are described throughout the specification.

Generally, in one embodiment the panel connector 126 is configured to receive a filter body portion of the inline water trap 110. The filter body portion is coupled to a filter input configured to receive a patient sample from a patient. In one embodiment a first cooperative element is a switch lever 152 of the panel connector 126, the switch lever 152 being a normally non-depressed switch. The filter body portion may act as a second cooperative element, configured to cooperate with the first cooperative element, where the filter body portion is configured to depress the switch lever 152 when it is properly engaged with the panel connector 126. The switch lever 152 is electrically coupled to the microprocessor 117, which monitors the state of the switch lever 152 to determine when the filter body portion, and thus the inline water trap, is properly engaged with the panel connector 126.

Figure 2:
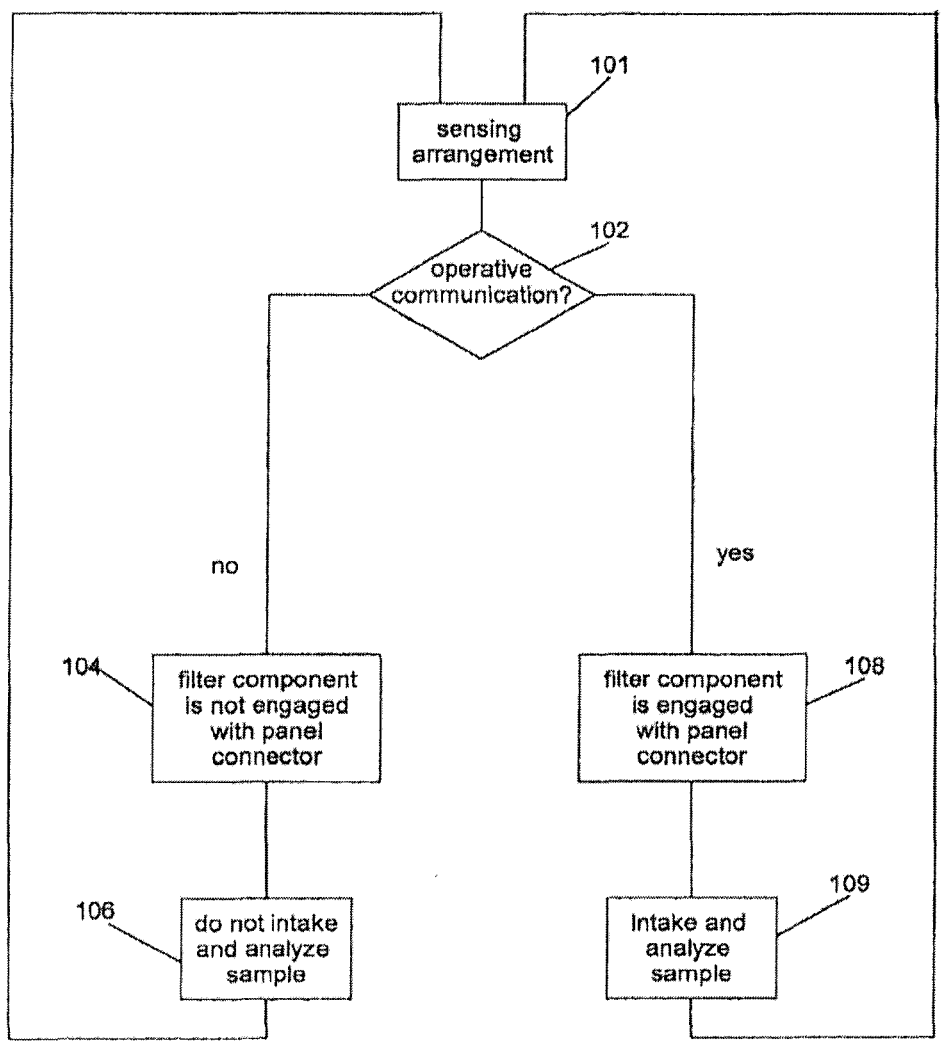

As is illustrated by the flow diagram of FIG. 2 and with reference to FIG. 1, in one embodiment the sensing arrangement 101 monitors to determine whether operative communication 102 has been established between the filter component 114 and the panel connector 126. For example, when operative communication has not be established, in one embodiment when the first cooperative element such as a switch lever is not depressed 102, this indicates to the microprocessor 117 of the respiratory gas monitor 128 that the filter component 114, and thus the inline water trap 110, is not engaged 104 with the panel connector 126, that there is no filtered patient sample being provided, and that the respiratory gas monitor 128 should not attempt to intake or analyze a sample 106.

When, however, operative communication between the filter component 114 and the panel connector 126 has been established, this indicates to the respiratory gas monitor 128 that the filter component 114 is properly engaged 108. This activates the respiratory gas monitor 128 and causes the respiratory gas monitor 128 to intake and analyze the filtered sample 109 provided by the filter component 114 and panel connector 126. In one embodiment, when the filter component 114 properly engages the panel connector 126, the filter component 114 depresses the switch lever 152. In this embodiment depression of the switch lever 152 indicates that operative communication has been established between the filter component 114 and the panel connector 126. Various suitable methods and apparatuses and various suitable cooperative elements for indicating whether operative communication 102 has been established between the filter component 114 and the panel connector 126 are envisioned.

In one embodiment, when the filter component 114 is again removed from the panel connector 126, the sensing arrangement 101 will determine that operative communication 102 between the filter component 114 and the panel connector 126 is no longer established and will indicate to the respiratory gas monitor 128 to discontinue intaking and analyzing 106. In one embodiment, removal of the filter component 114 from the panel connector will allow the switch lever 152 to once again return to its non-depressed state, causing the respiratory gas monitor 128 to discontinue intaking and analyzing 106.

Figure 3:
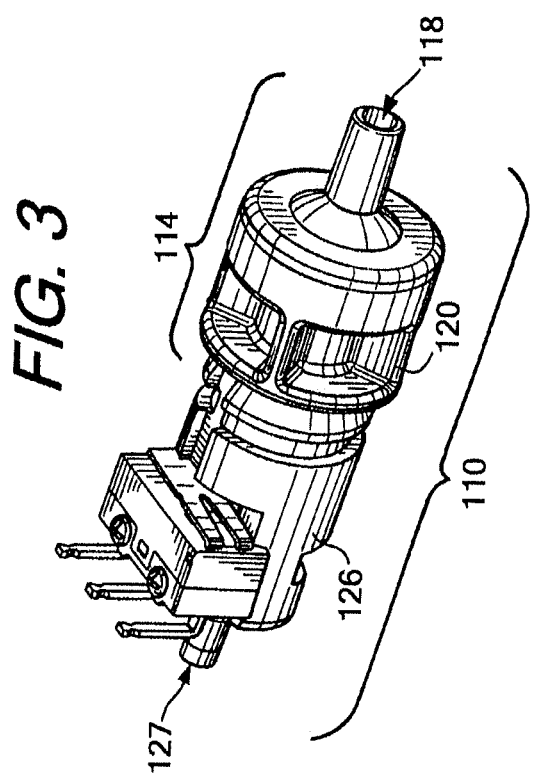
FIG. 3 is an isometric view of an assembled embodiment of the inline water trap of the present invention as illustrated in FIG. 1.

FIG. 3 generally illustrates one embodiment of an inline water trap 110 including the filter component 114. The filter component 114 includes a filter body 120 shown engaged with the panel connector 126. In FIG. 3, the panel connector 126 is illustrated removed from the respiratory gas monitor 128 (shown in FIG. 1). The inline water trap 110 is configured to receive a patient sample via a filter inlet 118. The panel connector 126 is in fluid communication with the gas monitoring and detection elements 115 (shown in FIG. 1) and is configured to supply filtered patient samples to the gas monitoring and detection elements 115 from a panel connector outlet 127.

As is generally illustrated in FIG. 4 and will be described in more detail below, one embodiment of the inline water trap 110 of the present invention includes a filter input 116, which defines the filter inlet 118, and a filter body 120 which defines a filter outlet 122.

As is illustrated in the exploded view of FIG. 4, in the illustrated embodiment the filter component 114 includes the filter input 116 and the filter body 120. The filter body 120 houses a porous filter, embodied in the illustrated embodiment as a hydrophilic pellet 130. Proximate the filter outlet 122, the filter body 120 includes a panel connector engagement portion 124 configured to engage the panel connector 126 associated with and coupled to the respiratory gas monitor 128.

With reference to the cross-sectional flow view of the inline water trap 110 shown in FIG. 5, the inline water trap 110 defines a flow path 134 from the filter inlet 118 to the gas monitoring and detection elements 115 (see FIG. 1). In the illustrated embodiment, the filter input 116 defines a central bore 132 in fluid communication with the filter inlet 118. The filter inlet 118 is configured to receive a patient sample through the filter inlet 118 and into the central bore 132.

The filter body 120 also defines a central bore 136. Disposed within the central bore 136 of the filter body 120 is the hydrophilic pellet 130. The filter body 120 includes a bore wall 138 that defines the central bore 136. In one embodiment, the hydrophilic pellet 130 is size such that its diameter is approximately equal to the diameter 143 of the central bore 136, and therefore, when the hydrophilic pellet 130 is disposed within the central bore 136, it is in operative contact with the bore wall 138 around the entire circumference of the central bore 136. Therefore, the hydrophilic pellet 130 is preferably held in place in the central bore 136 in a press-fit or interference fit configuration with the bore wall 138.

As is illustrated in FIG. 5, the bore wall 138 defines a shoulder portion 140 proximate the filter outlet 122. The portion of the hydrophilic pellet 130 proximate the filter outlet 122 rests against the shoulder portion 140 configured to axially locate the hydrophilic pellet 130 within the central bore 136. Additionally, the shoulder portion 140 defines a smaller diameter 141 than the diameter 143 of the portion of the central bore 136 proximate the filter input 116. Based on this configuration, a patient sample passing from the central bore 136, past the shoulder portion 140, and to the filter outlet 122 must pass through the hydrophilic pellet 130.

With reference also to FIG. 6, in one embodiment the bore wall 138 of the filter body 120 extends from the shoulder portion 140 past the hydrophilic pellet 130 receiving region to a radially outwardly projecting region 174 coupled to an axially projecting portion 178 at a junction 176.

As illustrated in FIG. 6, the filter input 116 includes an input bore wall 180 that extends axially towards the filter body 120 defining the filter input central bore 132. The input bore wall 180 extends into a transition junction 182 that transitions radially outwardly into a transverse wall portion 184. The transverse wall portion 184 extends radially outwardly from the transition junction 182 and terminates at an outer junction 186 between the transverse wall portion 184 and a filter body receiving wall 188. The filter body receiving wall 188 extends axially away from the outer junction 186 to the filter body axially locating portion 190.

As illustrated in FIG. 6, the axially projecting portion 178 of the filter body 120 is constructed with an interior diameter similar to the outer diameter of the filter body receiving wall 188 such that the axially projecting portion 178 is configured to snugly fit around the filter body receiving wall 188. When the filter body 120 is engaged with the filter input 116, the inner surface of the axially projecting portion 178 sits flush against the outer surface of the filter body receiving wall 188. The portion of the axially projecting portion 178 distal from the hydrophilic pellet 130 rests flush against the filter body axially locating portion 190.

In one embodiment, the filter input 116 is preferably formed from PTS Teflon with polyester backing. It is also contemplated that other suitable materials well-known in the art may be used to form the filter input 116.

In the embodiment illustrated in FIG. 6, the polyester of the filter input 116 may be heat staked to the filter body 120, securing the filter input 116 and the filter body 120 together. The filter input 116 may also be ultrasonically welded to filter body 120 at the interface between the axially projecting portion 178 of the filter body 120 and the filter input 116. It is also contemplated that the filter input 116 and the filter body 120 may be connected by other suitable means well-known in the art.

In the illustrated embodiment, the filter body 120 and the filter input 116 are formed as two separate pieces. These components may also be integrally formed by any means well-known in the art. In the embodiment illustrated in FIG. 6, the filter input 116 and the filter body 120 are formed as two separate pieces that are coupled together as illustrated.

In one embodiment, the hydrophilic pellet 130 is a gas permeable, liquid and solid impermeable element. Therefore, a patient sample containing gases, as well as liquid and possibly other solid contaminants, which encounters the hydrophilic pellet 130 is effectively filtered. The gas portion of the patient sample is allowed to pass through the hydrophilic pellet 130, and the liquid portion is partially stopped by and partially absorbed by the hydrophilic pellet 130. The solid portion is completely stopped by the hydrophilic pellet 130.

The hydrophilic pellet 130 may be formed from any suitable material known in the art. Additionally, though the porous filter is illustrated and described as a hydrophilic pellet 130, any other suitable porous gas permeable, liquid semi-impermeable or impermeable filter known in the art in any suitable shape.

Figure 7:
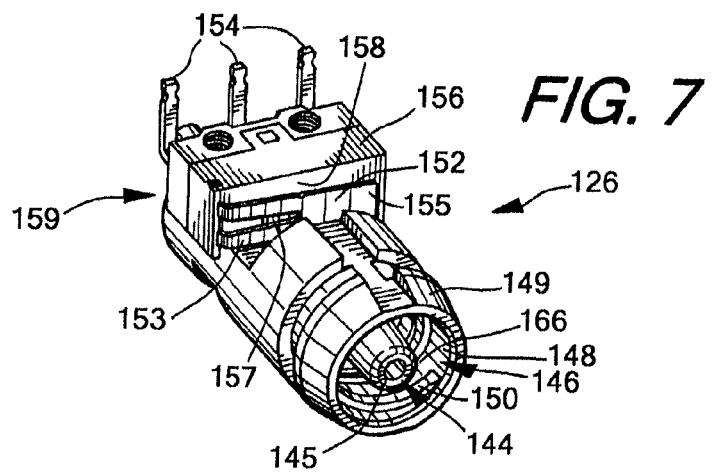
FIG. 7 is an isometric view of a panel connector including threading and a switch lever.
Figure 8:
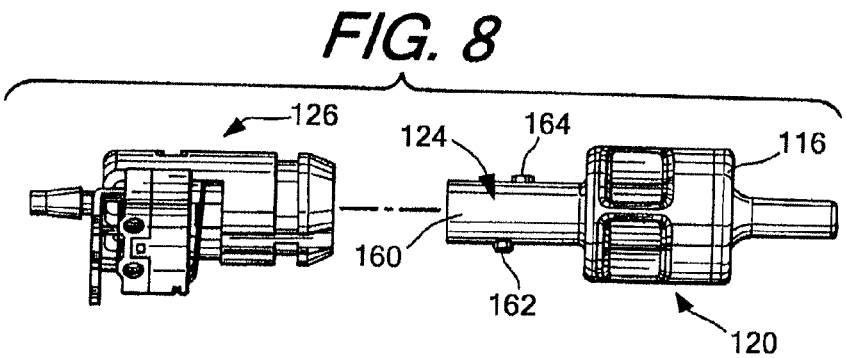
FIG. 8 is an isometric side exploded view of the filter body portion and panel connector of an embodiment of the inline water trap of FIGS. 1 and 3-7.

Referring to FIGS. 7 and 8, in one embodiment the filter body 120 includes a panel connector engagement portion 124 to couple the filter body to the panel connector 126. An exemplary embodiment of the panel connector 126 is illustrated in FIGS. 7 AND 8. The panel connector engagement portion 124 preferably includes a tubular portion 160 sized to fit around a panel connector central bore annular wall 145 and within the filter body receiving recess 146 as will be described. As illustrated in FIG. 8, the panel connector engagement portion 124 also includes a first projection or protrusion 162 and a second projection or protrusion 164. The protrusions 162, 164 extend radially outwardly from the tubular portion 160. The first protrusion 162 is preferably located on the opposite side of the tubular portion 160, one hundred and eighty degrees radially from the second protrusion 164. The first protrusion 162 is also axially offset from the second protrusion 164, with the first protrusion 162 axially proximate the panel connector 126 and the second protrusion 164 axially distal from the panel connector 126 and axially proximate the filter input 116.

In the embodiment illustrated in FIGS. 7 and 8, the first and second protrusions 162, 164 are configured to interact with threading 150 defined by the panel connector 126 (shown in FIG. 7), to couple the filter body 120 to the panel connector 126 as will be further described below. The threading 150 defines a channel 166 into which the first and second protrusions 162, 164 may be received.

Figure 9:
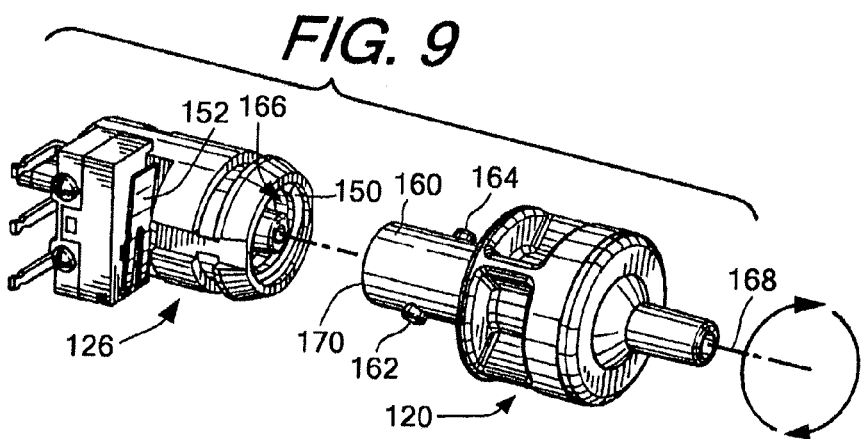
FIG. 9 is an isometric view of the filter body portion of an embodiment of the inline water trap of FIGS. 1, 3-6, and 8 positioned for engagement with the panel connector.

To assemble the filter body 120 with the panel connector 126, as illustrated in FIG. 9, the first protrusion 162 is preferably placed at the beginning of the channel 166 defined by the threading 150. To engage the filter body 120 with the panel connector 126, the filter body 120 is rotated about its longitudinal axis 168, urging the first protrusion 162 into and to follow the channel 166, and moving the second protrusion 164 into the channel 166 to follow the threading 150 with continued rotation of the filter body 120.

Figure 10:
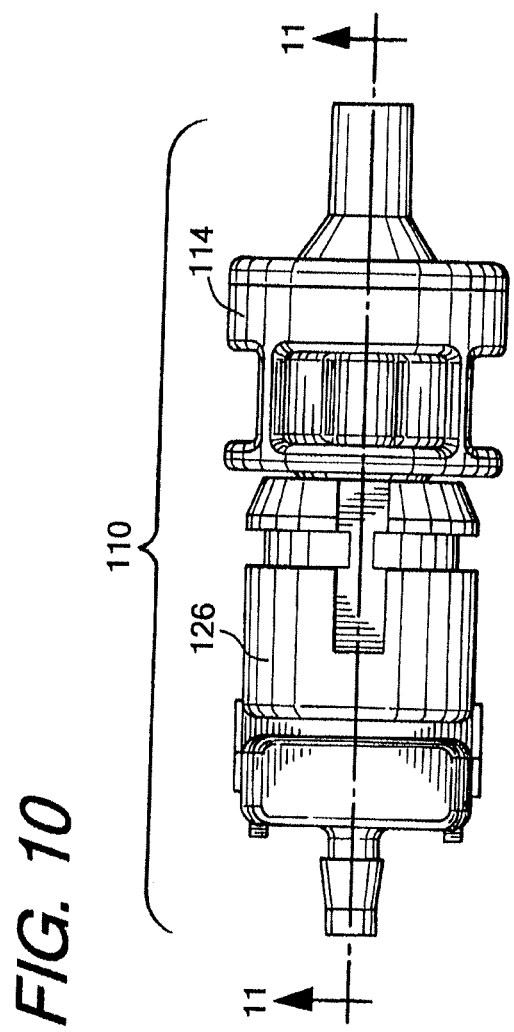
FIG. 10 is a top view of an embodiment of the inline water trap of FIGS. 1 and 3-9.

FIG. 10 illustrates a top view of an embodiment of the inline water trap 110 including the panel connector 126.

Figure 11:
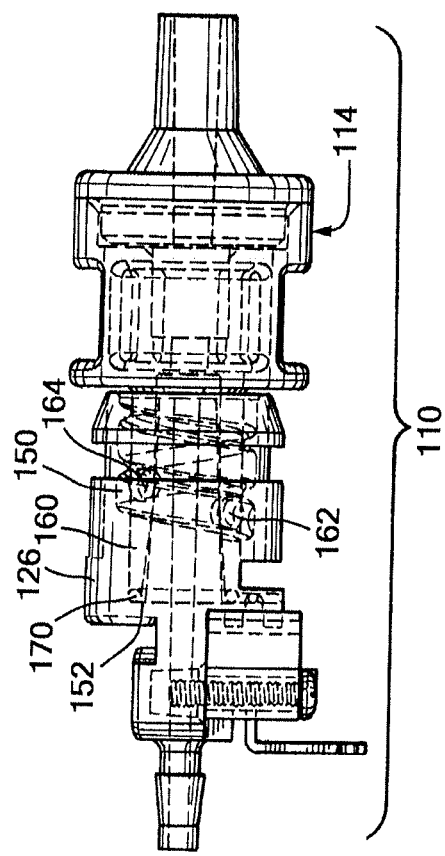
FIG. 11 is a view with portions transparent taken along line 11-11 in FIG. 10 of an embodiment of the inline water trap of FIGS. 1 and 3-10.

FIG. 11 is a view taken along line 11-11 in FIG. 10, with portions of the inline water trap 110 transparent to illustrate the threading 150 defined in the panel connector 126. The first and second protrusions 162, 164 are illustrated in the channel 166 engaged with the threading 150 with the filter body 120 properly engaged with the panel connector 126. The end wall 170 of the tubular portion 160 of the filter body 120 has engaged and depressed the switch lever 152.

Returning to FIG. 7, the panel connector 126 defines a filter body receiving recess 146 surrounding and concentric with the panel connector central bore 144 and separated from the panel connector central bore 144 by the panel connector central bore annular wall 145. The interior surface 148 of the panel connector 126 exterior wall 149 defines the threading 150 arranged and configured to be engaged by a portion of the filter body 120 (illustrated in FIG. 8). When the filter body 120 is engaged with the panel connector 126, the panel connector central bore 144 is placed in fluid communication with the fluid outlet 122 (not illustrated in FIG. 7).

In the embodiment illustrated in FIG. 7, the panel connector 126 further includes a switching mechanism 159, including a normally non-depressed switch lever 152. The switching mechanism 159 is electrically coupled to the microprocessor 117 (not illustrated in FIG. 7) through switch terminals 154, which electronically interface with the microprocessor 117.

The switching mechanism 159 includes the switch lever 152, which defines a first end 153 and a second end 155, and is coupled proximate the first end 153 to a switch housing 156, which defines a surface 158 extending transversely to the flow path 134 (not illustrated in FIG. 7). The switch lever 152 extends along and obliquely away from the surface 158, with the second end 155 located, in its normal non-depressed state, a distance from the surface 158.

With reference to FIG. 12, in one embodiment. The switching mechanism 159 includes a switch actuator 157 which projects from the switch housing 156 adjacent to the switch lever 152. When the second end 155 of the switch lever 152 is depressed towards the switch housing 156, the switch lever 152 actuates the switch actuator 157, causing the switching mechanism 159 to signal the microprocessor 117 (illustrated in FIG. 1).

FIGS. 13 and 14 illustrate partial cross-sectional views showing the filter body 120 as it rotated, thereby compressing the switch lever 152.

With reference to FIGS. 9, 11, 13, and 14, the filter body 120 is rotated until the end wall 170 of the tubular portion 160 reaches the normally non-depressed switch lever 152 and the end wall 170 engages the switch lever 152. Further rotation of the filter body causes the end wall 170 to urge the second end 155 of the switch lever 152 towards the surface 158 of the switch housing 156 until the switch lever 152 contacts the switch actuator 157, urging the switch actuator 157 towards the surface 158 and depressing the switch actuator 157. At this point, the filter body 120 is fully engaged with the panel connector 126 and the switch lever 152 is fully compressed, actuating the switch actuator 157, which actuates the switching mechanism 159, which signals the microprocessor 117 (illustrated in FIG. 1) that the filter body 120 is properly engaged.

Returning to FIG. 5, in the illustrated embodiment, the central bore 132 of the filter input 116 is in fluid communication with the central bore 136 of the filter body 120. Therefore, the central bores 132, 136 define the first portion of the flow path 134. Preferably, a patient sample passes through the central bore 132 of the filter input 116 and to the central bore 136 of the filter body 120.

In the illustrated embodiment, as the patient sample reaches the central bore 136 of the filter body 120, it reaches the hydrophilic pellet 130. Upon encountering the hydrophilic pellet 130, the hydrophilic pellet 130 selectively allows the gas portion of the patient sample to pass through to the filter outlet 122. The water and other contaminants contained in the patient sample are either absorbed by the hydrophilic pellet 130 or collect in the flow path 134 prior to the hydrophilic pellet 130 on the side of the hydrophilic pellet 130 proximate to the filter input 116. This is not problematic as the illustrated embodiment of the inline water trap 110 is designed for both drier patient samples (although it is envisioned that the inline water trap 110 may be used to filter patient samples with various moisture content), as well as single patient use (though, again, it is envisioned that the inline water trap 110 could be used for varying amounts of patients). Thus, preferably in the illustrated embodiment only small amounts of water and contaminants will collect in the flow path before the inline water trap 110 is disposed of and replaced with a new inline water trap 110.

If it is desired to use an embodiment of the inline water trap 110 to filter a wetter patient sample, it is possible to combine an embodiment of the inline water trap 110 with a dryer configured to dry the patient sample prior to entry into the inline water trap.

In one embodiment, the absorption of the liquid portion of the patient sample by the porous filter, embodied in one embodiment as the hydrophilic pellet 130, tends to make the porous filter swell. The porous filter is somewhat self-sealing and tends to become non-porous when it comes into contact with water. In the non-porous state, the porous filter tends to block the passage of both liquid and gas flow therethrough. Thus, if a significant amount of liquid is absorbed, the hydrophilic pellet 130 will block gas flow and must be replaced. Therefore, the hydrophilic pellet 130 will be even more snugly contained within the central bore 136 of the filter body 120, further preventing the patient sample from reaching the filter outlet 122 without passing through the hydrophilic pellet 130 (and also eventually causing the flow path to be completely closed, as is discussed further below).

If the porous filter absorbs a sufficient amount of water, the porous filter will completely or almost completely block the flow of gas therethrough. In such case, the lack of the expected amount of gas being supplied to the respiratory gas monitor 128 will indicate to an operator that the porous filter has been blocked and that the filter component 114 should be changed. However, other suitable automatic detection mechanisms for determining and indicating when the filter component 114 should be changed or when the porous filter has become gas impermeable are also envisioned.

Figure 15:
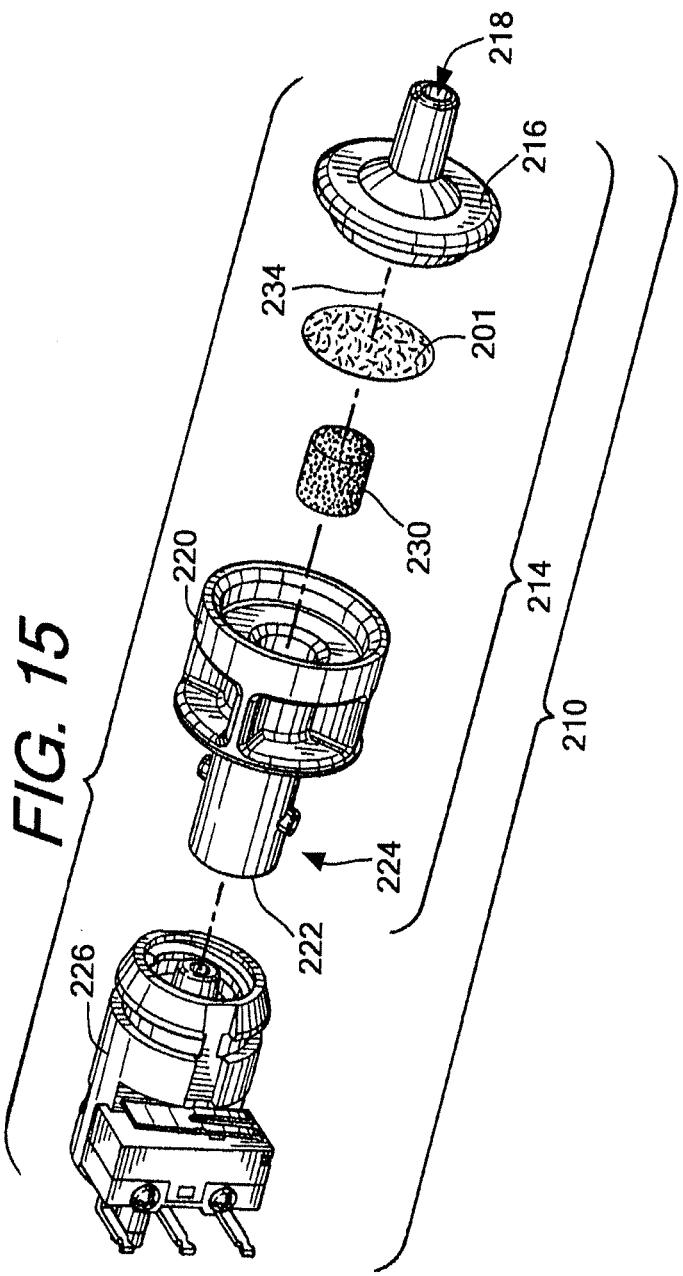
FIG. 15 is an exploded view of a second embodiment of the inline water trap of the present invention.

FIG. 15 illustrates an alternate embodiment of an inline water trap 210 of the present invention. The inline water trap 210 includes a filter component 214 and a panel connector 226 that can be similar to or identical with filter component 114 and panel connector 126 of the inline filter 110 described above with reference to FIGS. 1-14, for example. Accordingly, elements of the inline water trap 210 have been given the same reference number as corresponding elements of the inline trap filter 110, but incremented by "100". In addition, the inline water trap 210 includes a hydrophobic filter 201 disposed within the flow path 234. The hydrophobic filter 201 is arranged and configured upstream of the hydrophilic pellet 230. Preferably, the hydrophobic filter 201 is a gas permeable, liquid impermeable filtering disk through which the patient sample must pass to reach the hydrophilic pellet 230. As will further described below, a patient sample enters the filter input 216 through the filter inlet 218 and passes through the filter input 216. The patient sample reaches the hydrophobic filter 201, where only the gas portion of the patient sample is allowed to pass and continue along the flow path 234, while any water or other contaminants remains on the upstream side of the hydrophobic filter 201 proximate the filter input 216. The portion of the patient sample that passes through the hydrophobic filter 201 then reaches the hydrophilic pellet 230. As in the previous embodiment, the hydrophilic pellet 230 only permits the gas portion of the patient sample to pass through to the filter outlet 222, while absorbing at least a portion of the water contained within the sample and preventing water and other contaminants from passing through to the filter outlet 222.

The filter body 220 including a panel connector engagement portion 224 engages the panel connector 226 similarly to the previous embodiment. The hydrophilic pellet 230 and the hydrophobic filter 201 are both retained within the filter body 220.

Figure 16:
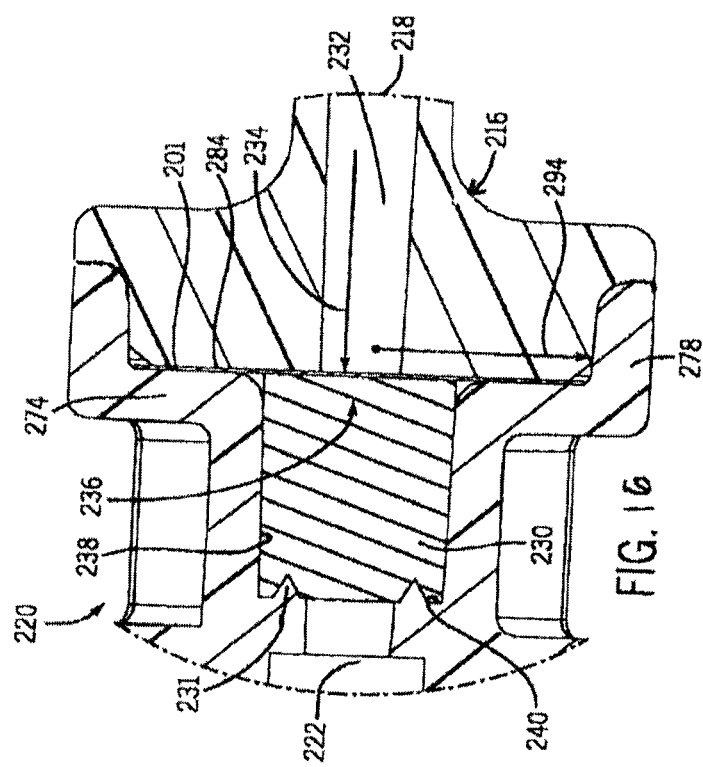
FIG. 16 is a detailed cross-sectional view of the connection between the filter body and the filter input of a second embodiment of the inline water trap of FIG. 15 including an alternate bore and a hydrophobic filter.

FIG. 16 illustrates the alternate embodiment of the inline water trap including the hydrophobic filter 201 and the hydrophilic pellet 230 disposed within the filter body 220. This alternate embodiment provides additional sealing of the filter outlet 222 to liquid or contaminants by preventing these from shunting around the outside of the hydrophilic pellet 230.

As in the previous embodiment, the hydrophilic pellet 230 may be press fit into the filter body central bore 236. The filter body central bore 236 is again defined by a bore wall 238. The bore wall 238 again includes a shoulder portion 240. Unlike the previous embodiment, however, the shoulder portion 240 defines an axially extending annular ridge 231. The annular ridge 231 surrounds the filter outlet 222 and extends axially away from the shoulder portion 240. Preferably, the hydrophilic pellet 230 is somewhat flexible and thus deforms around the annular ridge 231, sealing the central bore 236 from the filter outlet 222. Thus, if any water or other contaminants circumvent the hydrophilic pellet 230 along the bore wall 238, the annular ridge 231 forces the water and contaminants away from the filter outlet 222, towards the hydrophilic pellet 230, thereby preventing these from reaching the filter outlet 222.

Figure 17:
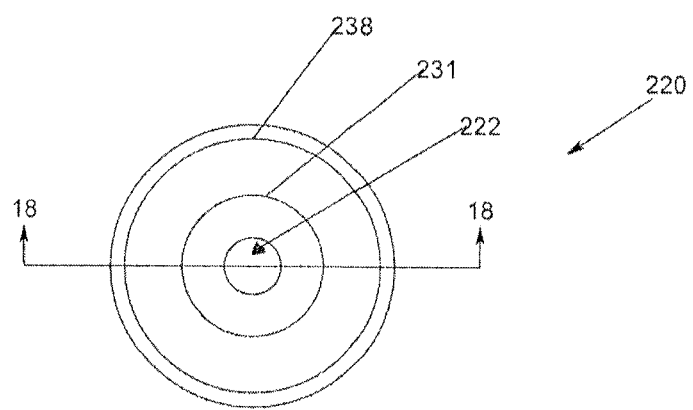
FIG. 17 is a top plan cross-sectional view of the bore of the filter body of a second embodiment of the inline water trap of FIGS. 15 and 16.

FIG. 17 illustrates a cross-sectional view of the second embodiment of the filter body 220 looking directly down the flow path 234 (illustrated in FIG. 15) of the bore wall 238, the filter outlet 222, and the annular ridge 231.

Figure 18:
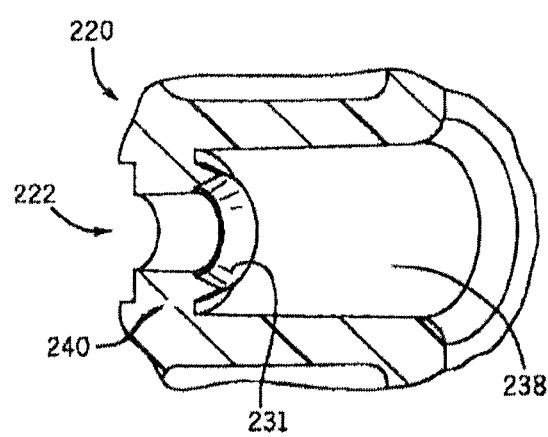
FIG. 18 is a side cross-sectional view, taken along line 18-18 of FIG. 17, of the bore of the filter body of a second embodiment of the inline water trap of FIGS. 15-17.
Figure 19:
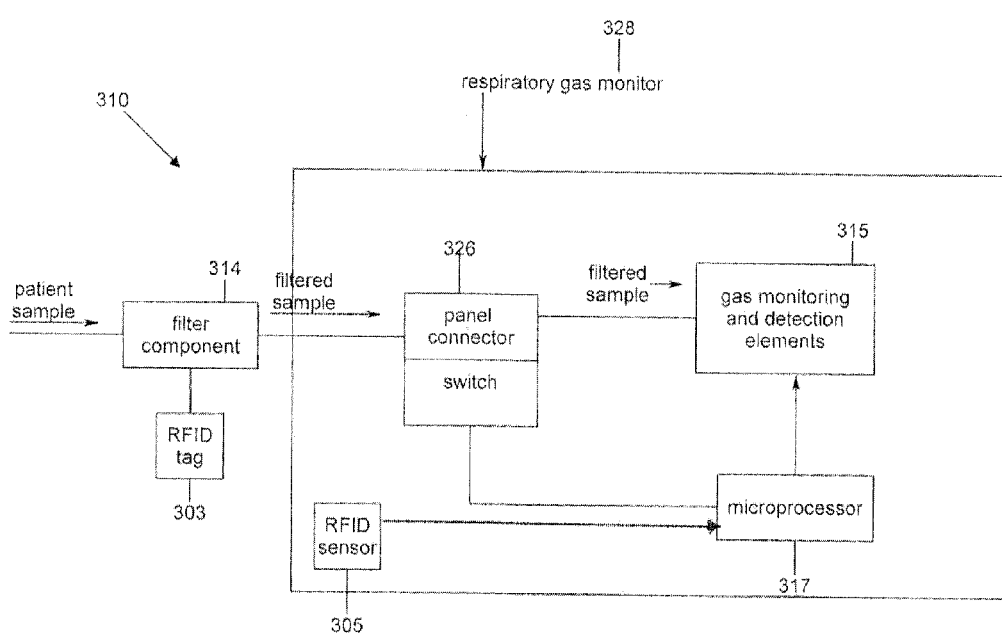
FIG. 19 is system block diagram showing a third embodiment of the inline water trap of the present invention coupled to a respiratory gas monitor.

FIG. 18 illustrates a cross-sectional view taken along the line 18-18 of FIG. 17, illustrating the second embodiment of the filter body 220 with the hydrophilic pellet 230 removed. As is illustrated, the annular ridge 231 extends axially upstream and away from the shoulder portion 240 essentially forming a ridge surrounding the filter outlet 222 and assisting to prevent any water or contaminants from bypassing the hydrophilic pellet 230 and passing through to the filter outlet 222.

Returning to FIG. 16, the hydrophilic pellet 230 is substantially cylindrical and extends in the filter body central bore 236 axially from the shoulder portion 240 towards the filter input 216. The porous filter, embodied in this embodiment as the hydrophilic pellet 230 (although embodiments of other suitable porous filters are envisioned), is somewhat self-sealing and tends to become non-porous when it comes into contact with water. In the non-porous state, the porous filter tends to block the passage of both liquid and gas flow therethrough. Thus, if a significant amount of liquid is absorbed, the hydrophilic pellet 230 will block gas flow and must be replaced. Therefore, it can be advantageous in some applications to include the hydrophobic filter 201 to prevent the hydrophilic pellet 230 from contacting water and blocking the flow path 234.

The hydrophobic filter 201 of the alternate embodiment is preferably of the type disclosed in U.S. Pat. Nos. 6,923,847 and 7,402,197 of Larsen et al., assigned to Criticare Systems, Inc., which are incorporated herein, in their entirety, by reference. It is also envisioned that other suitable types of hydrophobic filters known in the art may be used.

In one embodiment, the hydrophobic filter 201 may be a membrane filter element, such as GORE-TEX expanded polytetrafluoroethylene (PTFE) laminate having a one micron pore size on spun-bonded polyester, with the PTFE laminate surface proximate the filter input 216.

In the embodiment illustrated in FIG. 16, the hydrophobic filter 201 is preferably a disk with a radius less than or equal to the interior radius 294 of the axially projecting portion 278 of the filter body 220. The hydrophobic filter 201 is preferably permanently coupled to the radially outwardly projecting portion 274 of the filter body 220 by means of heat staking or any other suitable attachment method known in the art. The filter input 216 is preferably also configured such that the transverse wall portion 284 of the filter input 216 abuts against an annular portion of the hydrophobic filter 201 pinning the annular portion of the hydrophobic filter 201 not disposed within the flow path of the patient sample against the radially outwardly projecting portion 274 of the filter body 220.

In the alternate embodiment illustrated in FIG. 16, a patient sample enters the filter inlet 218 and passes through the filter input 216 through the filter input central bore 232. The patient sample then encounters the hydrophobic filter 201. The hydrophobic filter 201 allows the gas portion of the patient sample to pass through, but blocks the passage of the water and contaminants contained within the patient sample. The portion of the patient sample that passes through the hydrophobic filter 201 then encounters the hydrophilic pellet 230 as it enters the filter body central bore 236. The hydrophilic pellet 230 absorbs any water remaining in the filtered patient sample and blocks any other contaminants from passing, allowing only the gas portion of the patient sample to pass through the filter body central bore 236 and through to the panel connector 226 (illustrated in FIG. 15). Therefore, this alternate embodiment provides two filtering mechanisms useful for preventing certain embodiments of hydrophilic pellets 230 from absorbing large amounts of water and becoming gas impermeable.

In some embodiments the respiratory gas monitor 128 (illustrated in FIG. 1) is sensitive to water and contaminants and expensive to repair or replace. Thus, having multiple filtering mechanisms may be desirable in some applications and embodiments.

The configuration illustrated in FIG. 16 including both the alternate hydrophilic pellet 230 and the hydrophobic filter 201 is merely exemplary. Various other suitable configurations are envisioned. The filter body central bore 236 may be used with or without the hydrophobic filter 201. Additionally, the first embodiment of the filter body central bore 136 may be used in conjunction with the hydrophobic filter 201.

In a second alternate embodiment, it may be desirable to provide a system to verify that the correct type of filter component 314 has been coupled to the panel connector 326. Therefore, a Radio Frequency Identification (RFID) tag 303 may be coupled to or integrally formed with the filter component 314, the filter input of the inline water trap, or any other appropriate portion. The RFID tag 303 may be active, passive, battery-assisted passive, optical, or any other suitable type of RFID tag 303 known in the art.

In one embodiment, an RFID sensor 305 is electrically integrated with, coupled to, or otherwise integrated with the respiratory gas monitor 328. The microprocessor 317 periodically sends an interrogate signal. When a filter component 314 with the proper RFID tag 303 is in range and/or coupled to the panel connector 326, the RFID tag 303 responds to this interrogate signal with a coded RFID signal. The RFID sensor 305 receives this coded RFID signal and signals to the respiratory gas monitor 328 that the correct type of filter component 314 is engaged with the panel connector 326. The RFID sensor 305 indicates to the microprocessor 317 to enable the gas monitoring and detection elements 315 to intake and analyze the provided filtered patient sample. Unless the RFID sensor 305 indicates to the respiratory gas monitor 328 that the correct type of inline water trap 314 is engaged, the microprocessor 317 does not allow the gas monitoring and detection elements 315 to intake or analyze a sample. This prevents the respiratory gas monitor 328 from intaking a wet or contaminated patient sample, thus protecting the respiratory gas monitor 328 from damage.

It is envisioned that this embodiment including the RFID tag 303 and RFID sensor 305 may include all or any features of each of the other two embodiments. This embodiment may or may not contain the switching mechanism described above. If this embodiment is used in conjunction with the switching mechanism of the previous two embodiments it provides additional benefits of a second verification system that the correct type of filter component has been installed, meaning that the respiratory gas monitor 328 and its components will be protected and that the proper filter component 314 has be engaged with the panel connector 326.

For purposes of this disclosure, the term "coupled" means the mechanical joining of two components directly or indirectly to one another. Such joining may be stationary in nature or moveable in nature. Such joining may be achieved with the two components and any additional intermediate members being integrally formed as a single unitary body with one another or the two components and any such additional member being attached to one another. Such adjoining may be permanent in nature or alternatively be removable or releasable in nature.

For purposes of this disclosure, the term "contaminants" means any liquid, mucous, or solid damaging to the respiratory gas monitor. For purposes of this disclosure, the term "actuate" and variations thereof mean any type of actuation, including but not limited to mechanical actuation and electrical actuation, as well as any other suitable type known in the art.

The inline water trap of the present invention is of a construction which is both durable and long lasting, and it should also require little or no maintenance to be provided by the user throughout its operating lifetime. The inline water trap of the present invention is also of relatively inexpensive construction to enhance its market appeal and to thereby afford it the broadest possible market. Finally, the inline water trap of the present invention achieves all of the aforesaid advantages and objectives without incurring any substantial relative disadvantage.

Although the foregoing description of the inline water trap and method of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the inline water trap and method of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the inline water trap and method of the present invention as determined by the appended claims when interpreted in accordance with the breadth to which they are fairly, legally, and equitably entitled.

What is claimed is:

1. An inline water trap, including a panel connector of a respiratory gas monitor, the inline water trap comprising:
   a filter component defining a bore, the filter component including a filter body including a filter inlet and a filter outlet in fluid communication through the bore, the filter component further including a panel connector engagement portion; and
   a filter element disposed within a first portion of the bore, the filter element configured to allow gas to pass through the bore while preventing at least one of water and contaminants from passing through the bore.

2. An inline water trap comprising:
   a filter input including an input bore wall, the input bore wall defining a first central bore, the input bore wall extending to a transition junction that transitions radially outward to a transverse wall portion, the transverse wall portion terminating at an outer junction between the transverse wall portion and a filter body receiving wall;
   a filter body having a bore wall which defines a second central bore, the bore wall extending from a shoulder portion to a radially outward projecting region coupled to an axially projecting portion at a junction;
   wherein the axially projecting portion of the filter body has an inner diameter substantially similar to an outer diameter of the filter body receiving wall of the filter input, such that the axially projecting portion sits on the filter body receiving wall when the filter body is engaged with the filter input.

3. The inline water trap of claim 2 further comprising a filter element, the filter element being disposed within the second central bore, the filter element having an outer diameter substantially equal to an inner diameter of the second central bore.

4. The inline water trap claim 3 wherein the filter element abuts the shoulder portion of the filter body when the filter element is disposed within the second central bore.

5. The inline water trap of claim 4 wherein the shoulder portion defines a shoulder bore, the shoulder bore having a smaller diameter than the inner diameter of the second central bore.

6. The inline water trap of claim 5 wherein the shoulder bore, the second central bore, and the first central bore are all axially aligned, the shoulder bore, the second central bore, and the first central bore all defining a bore.

7. The inline water trap of claim 6 wherein the filter element is axially aligned with the shoulder bore, the second central bore, and the first central bore.

8. The inline water trap of claim 5 further comprising a filter outlet, the filter outlet being in fluid communication with the second central bore through the shoulder bore.

9. The inline water trap of claim 8 further comprising a panel connector engagement portion, the panel connector engagement portion being configured to engage a panel connector.

10. An inline water trap, including a panel connector of a respiratory gas monitor, the inline water trap comprising:
a filter input including an input bore wall, the input bore wall defining a first portion of a bore, the input bore wall extending to a transition junction that transitions radially outward to a transverse wall portion, the transverse wall portion terminating at an outer junction between the transverse wall portion and a filter body receiving wall;
a filter body having a bore wall which defines a second portion of the bore, the bore wall extending from a shoulder portion to a radially outward projecting region coupled to an axially projecting portion at a junction, the filter body further including a panel connector engagement portion;
a panel connector, the panel connector defining a third portion of the bore;
wherein the axially projecting portion of the filter body has an inner diameter substantially similar to an outer diameter of the filter body receiving wall of the filter input, such that the axially projecting portion sits on the filter body receiving wall when the filter body is engaged with the filter input, and the panel connector portion of the filter body is configured to engage the panel connector.

11. The inline water trap of claim 10 wherein the shoulder portion of the filter body defines a fourth portion of the bore, the fourth portion of the bore having a smaller diameter than an inner diameter of the second portion of the bore.

12. The inline water trap of claim 11 further comprising a filter outlet, the filter outlet being in fluid communication with the second portion of the bore through the fourth portion of the bore, and placing the fourth portion of the bore in fluid communication with the third portion of the bore.

13. The inline water trap of claim 12 wherein the first portion of the bore, the second portion of the bore, the third portion of the bore, and the fourth portion of the bore are all axially aligned.

14. The inline water trap of claim 13 further comprising a filter element, the filter element being disposed within the second portion of the bore, the filter element having an outer diameter substantially equal to the inner diameter of the second portion of the bore.

15. The inline water trap claim 14 wherein the filter element abuts the shoulder portion of the filter body when the filter element is disposed within the second portion of the bore.

16. The inline water trap of claim 14 wherein the filter body is axially aligned with the first portion of the bore, the second portion of the bore, the third portion of the bore, and the fourth portion of the bore.

17. The inline water trap of claim 1 wherein
the filter body includes a bore wall which defines the first portion of the bore, the bore wall extending from a shoulder portion to a radially outward projecting region coupled to an axially projecting portion at a junction; and
the filter input includes an input bore wall, the input bore wall defining a second portion of the bore, the input bore wall extending to a transition junction that transitions radially outward to a transverse wall portion, the transverse wall portion terminating at an outer junction between the transverse wall portion and a filter body receiving wall;
wherein the axially projecting portion of the filter body has an inner diameter substantially similar to an outer diameter of the filter body receiving wall of the filter input, such that the axially projecting portion sits on the filter body receiving wall when the filter body is engaged with the filter input, and the panel connector portion of the filter body is configured to engage the panel connector.

18. The inline water trap of claim 17 wherein the shoulder portion of the filter body defines a third portion of the bore, the third portion of the bore having a smaller diameter than an inner diameter of the second portion of the bore.

19. The inline water trap of claim 17 wherein the filter element has an outer diameter substantially equal to an inner diameter of the first portion of the bore.

20. The inline water trap claim 1 wherein the filter element abuts the shoulder portion of the filter body when the filter element is disposed within the first portion of the bore.

\* \* \* \* \*